(12) United States Patent
Courvoisier et al.

(10) Patent No.: US 9,095,398 B2
(45) Date of Patent: Aug. 4, 2015

(54) TWO-PART DENTAL COMPONENT

(75) Inventors: Stephane Courvoisier, Basel (CH); Jost Lussi, Basel (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 14/117,494

(22) PCT Filed: May 31, 2012

(86) PCT No.: PCT/EP2012/002303
§ 371 (c)(1),
(2), (4) Date: Mar. 24, 2014

(87) PCT Pub. No.: WO2012/163528
PCT Pub. Date: Dec. 6, 2012

(65) Prior Publication Data
US 2014/0205970 A1    Jul. 24, 2014

(30) Foreign Application Priority Data
Jun. 1, 2011    (EP) ..................................... 11004473

(51) Int. Cl.
*A61C 8/00*    (2006.01)
(52) U.S. Cl.
CPC .............. *A61C 8/0089* (2013.01); *A61C 8/005* (2013.01); *A61C 8/0062* (2013.01); *A61C 8/0068* (2013.01)
(58) Field of Classification Search
CPC ... A61C 8/0062; A61C 8/0068; A61C 8/0089
USPC .................................................. 433/173, 174
See application file for complete search history.

(56) References Cited

U.S. PATENT DOCUMENTS

| 5,195,891 | A | | 3/1993 | Sule |
| 5,569,037 | A | * | 10/1996 | Moy et al. ...................... 433/173 |
| 5,662,473 | A | | 9/1997 | Rassoli et al. |

(Continued)

FOREIGN PATENT DOCUMENTS

| EP | 1139906 B1 | 12/1999 |
| EP | 1943978 A1 | 7/2008 |

(Continued)

OTHER PUBLICATIONS

International Search Report and Written Opinion in PCT/EP2012/002303.

*Primary Examiner* — Ralph Lewis
(74) *Attorney, Agent, or Firm* — Novak Druce Connolly Bove + Quigg LLP

(57) ABSTRACT

Secondary component for connection to a dental implant having an internal bore, said secondary component having a head part and a base part, the head part including a coronal portion which in use protrudes from the dental implant, and, apical of the coronal portion, an attachment portion, the base part including implant connection means for connection to an implant and fastening means, wherein the attachment portion and fastening means can be directly coupled together in a rotatable manner in order to axially join the head and base parts together, while still enabling the base part to be rotated relative to the head part such that the implant connection means can engage the implant and secure the secondary component to this, the head part further including a through passage extending from the coronal portion to the attachment portion and the base part including drive means which, when the head and base parts are coupled together, is in communication with this passage.

25 Claims, 9 Drawing Sheets

(56) References Cited

U.S. PATENT DOCUMENTS

| | | |
|---|---|---|
| 6,419,492 B1 | 7/2002 | Schroering |
| 8,033,826 B2 * | 10/2011 | Towse et al. .................. 433/172 |
| 2002/0031748 A1 | 3/2002 | Crudo |
| 2010/0196853 A1 | 8/2010 | Zipprich et al. |
| 2010/0203476 A1 | 8/2010 | Studer et al. |

FOREIGN PATENT DOCUMENTS

| | | |
|---|---|---|
| EP | 2005915 A1 | 12/2008 |
| EP | 2036515 A1 | 3/2009 |
| FR | 2747032 A1 | 10/1997 |

* cited by examiner

TWO-PART DENTAL COMPONENT

FIELD OF INVENTION

This invention relates to a two part dental component, in particular a dental abutment, for use in combination with a dental implant. The component consists of one part which in use protrudes from the implant and which carries out the main function of the component and another part for firmly securing the component to the implant.

BACKGROUND

Dental implants are used to replace individual teeth or for anchoring more complex structures, which generally replace several or even all of the teeth. The materials used for dental implants are often titanium and alloys thereof, and increasingly ceramic materials. These materials have the necessary strength for withstanding the mechanical loads that occur, and they are at the same time sufficiently biocompatible for osseointegration and long term use in the mouth.

Implants are often constructed in two parts, in which case they consist of an anchoring part, often referred to in isolation as the implant, and of a separate abutment. The anchoring part is either embedded completely in the bone, that is to say to the height of the alveolar crest, or protrudes by a few millimeters from the alveolar crest into the soft tissue. The abutment is mounted on the anchoring part either after the latter has become incorporated (osseointegrated) into the bone or directly after the anchoring part has been inserted. It can also be attached to the anchoring part prior to insertion. Most usually the abutment is not mounted until after osseointegration. In such cases a component called a healing cap is often mounted to the implant during the osseointegration process to prevent incursion of soft tissue over the implant site. Ultimately, the desired prosthetic element (e.g. bridge or crown) is connected to the abutment. The prosthetic element can be adhesively bonded, cemented, screwed or directly veneered onto the abutment.

It is also possible for the implant to be constructed in one part, such that the anchoring part and the abutment are produced in one integral piece. Hence in such implant systems the integrated anchoring part and abutment are always positioned within the mouth at the same time.

In contrast to one piece implants, two-part implants are more versatile, because the anchoring part and the abutment can be adapted to individual requirements. In particular the abutment shape and angulation, relative to the anchoring part, can be selected after implant insertion. This provides the surgeon with more flexibility and room for error in the placement of the implant. An additional advantage of two-part implants is that the abutment can be made from a different material than the anchoring part.

Due to their versatility two part dental implants are more commonly used than one-piece implants, and it is this form of implant with which the present invention is concerned. For the remainder of this specification therefore, the term "implant" will be used to denote the anchoring part of a two part implant, namely, the element which in use is anchored within the bone, and the term "secondary component" will be used to denote a component which is, in use, fastened to the implant and which protrudes from this into and in some cases through the gum. The secondary component can be an abutment, which provides support for a dental prosthesis, or in some instances may comprise an integrated abutment and final prosthesis. It can also be a component which is temporarily fixed to the implant such as a healing cap or impression post.

All secondary components must be capable of being firmly fastened to the implant in order to prevent loosening and potential loss of the component. This can be achieved in numerous ways, for example, via compression fit or cementing. However, screw fit connections are generally preferred. By applying a sufficiently high torque during attachment a firm connection between the implant and secondary component can be achieved.

In some systems therefore the implant comprises an internally threaded bore, while the secondary component comprises a corresponding apical thread, thus allowing the secondary component to be screwed directly into the implant. However, this has the disadvantage that the exact angular position of the secondary component relative to the implant is not known until final fixation. This can have disadvantages, particularly in relation to abutments used to support a single tooth prosthesis.

Therefore, many implant systems comprise anti-rotation means, which prevent relative rotation between the implant and abutment, or other secondary component, and which set a finite number of rotational positions which the secondary component can have relative to the implant.

These anti-rotation means consist of complementary non-circular portions in the implant and secondary component, usually having a polygonal shape such as a hexagon or octagon. For example, the internal bore of the implant may comprise a section having a hexagonal cross-section, while the abutment or other secondary component comprises a portion having an equivalent hexagonal cross-section. Alternatively the implant may comprise a male polygonal boss protruding from its coronal end, which in use is accommodated within a correspondingly shaped polygonal cavity within the secondary component.

Such systems ensure that the exact rotational position of the abutment or other secondary component in relation to the implant is known prior to fixation and can help to prevent loosening of the abutment during the lifetime of the implant.

Of course, when such anti-rotation means are employed it is not possible to rotate the secondary component relative to the implant and hence the secondary component can no longer be directly screwed into the implant. Therefore a third component, often a screw known as a "basal screw", is used to connect the secondary component to the implant.

When a basal screw is used the abutment or other secondary component typically comprises a screw channel extending through the component and having a screw seat. This enables the basal screw to be fed through the secondary component until the screw head abuts the screw seat and for a screwdriver to be inserted into the channel to connect to the screw and fasten this to the threaded bore of the implant.

An example of such a known implant system can be found for instance in US2002/0031748.

One problem with such systems is that the screw channel weakens the abutment by reducing its volume. Although this effect can be reduced by keeping the screw channel width to a minimum, the screw channel diameter is set by the diameter of the screw. This in turn must be sufficiently large to ensure that the screw is strong enough to withstand the torque and bending forces that will be placed on this firstly during assembly and then later during the use of the implant system, when strong masticatory forces will be experienced. This therefore limits the ability to reduce the screw channel width.

The need to prevent interference with existing teeth and to reduce bone loss limits the diameter of the implant (anchoring part) and hence also the apical end of the secondary component which is fastened to the implant. This is especially true when the apical end of the abutment is sized to be inserted into the implant. For this reason, the screw seat is usually positioned higher within the secondary component, where the volume is greater and can thus better withstand the weakening effect of the largest diameter section of the screw channel, namely that above the screw seat. This necessitates a longer screw shaft length and hence higher bending forces being experienced by the screw during use. The width of the screw channel also places restrictions on the minimal shape of the abutment, which limits the possibilities for grinding the abutment into an individualised, patient-specific shape.

The above problems are of particular concern in relation to ceramic abutments. Such abutments have high aesthetic benefits due to their colouring. However, these materials are brittle and prone to chipping, particularly in thin walled areas.

EP2036515 discloses an abutment in which the screw is held within the screw channel of the abutment by a metal inlay, which reduces the diameter of the screw channel above the screw head and prevents the screw from falling out. EP1139906 discloses a similar system in which the inlay is located at the apical end of the screw channel, below the screw head.

In both of these systems the abutment and screw form a three part assembly, wherein the final element, the inlay, is attached only after the screw has been inserted into the abutment. While these systems enable the screw to be retained within the abutment prior to connection to the implant, their ability to reduce the screw channel width and increase abutment strength is limited.

Both of these systems still require the provision of a coronal screw channel having a width great enough to enable a screwdriver head to pass through and engage with a standard basal screw head. Further, the provision of a separate inlay increases the cost and complexity of the abutment. In addition EP2036515 does not solve the problem of decreasing the minimal shape of the abutment, as for stability the inlay must remain encased within the coronal end of the abutment. As regards EP1139906, the inlay effectively forms the screw seat in this arrangement and thus is subject to high tensile stresses which can lead to damage of the inlay.

SUMMARY OF THE INVENTION

The object of at least a preferred embodiment of the present invention is to provide a secondary component, in particular an abutment, for use with a dental implant in which the diameter of the screw channel can be reduced, thus creating a secondary component having increased strength, without increasing the number of components of the system.

According to one aspect the present invention therefore provides a secondary component for connection to a dental implant having an internal bore, said secondary component comprising a head part and a base part, the head part comprising a coronal portion which in use protrudes from the dental implant, and, apical of the coronal portion, an attachment portion, the base part comprising implant connection means for connection to an implant and fastening means, wherein the attachment portion and fastening means can be directly coupled together in a rotatable manner in order to axially join the head and base parts together, the head part further comprising a through passage extending from the coronal portion to the attachment portion and the base part comprising drive means which, when the head and base parts are coupled together, is in communication with this passage.

By "directly coupled" it is meant that the head and base part are joined together without the need for additional components, such as an inlay. The coupling occurs through the interaction between the attachment portion of the head part and fastening means of the base part and holds the two parts in axial alignment. While in the coupled state the head and base part are thus axially joined together, although some play in the axial direction is possible in some embodiments.

The head and base parts are arranged to couple together in a rotatable manner, such that at least partial relative rotation between the parts is possible in their coupled state.

The present invention therefore provides a two-part secondary component, the base part of which can rotate relative to the head part. In effect the two part secondary component can be considered as a secondary component with an in-built implant connection means. As the implant connection means is directly coupled to the apical end of the secondary component this does not need to be passed through or accommodated within the through passage of the head part of the secondary component.

Therefore, this through passage need only be sized to enable a driving tool to be inserted for engagement with the drive means of the base part. The diameter of the passage through the secondary component can therefore be greatly reduced. The resulting increase in volume strengthens the secondary component. In addition, this reduction in passage diameter increases the ability to grind the coronal portion of the component into individualised shapes. Also, as there is no separate screw component, the risk of contamination or aspiration caused by the handling of this small component is eliminated.

The direct coupling of the head part and base part results in a simple construction. As no inlay or other third component is required to hold the parts together the connection between these is less liable to loosen or weaken over time.

The attachment portion and fastening means co-operate with one another to axially connect the head and base parts while still allowing them to at least partially rotate relative to one another about the longitudinal axis of the base part.

The attachment portion and fastening means form preassembled pieces of the head and base parts respectively. The attachment portion and/or the fastening means could be glued, bonded, moulded or otherwise permanently joined to the head and base parts respectively during manufacture, prior to the coupling of these two parts. In accordance with the present invention however, no additional component must be added to either the head or base part after these have been placed in contact with one another in order to enable coupling to occur.

For ease of construction and increased structural integrity the head and base parts are each preferably formed of one piece, i.e. these are each integral components. These parts can be formed by known methods, e.g. sintering, injection moulding, machining etc. It is also possible for only one of these components to be integrally formed.

In some embodiments, direct coupling may be achieved via modification or alteration of the attachment portion and/or fastening means after these components are placed in contact. In other words, although no additional elements are added to the assembly to enable coupling, the pre-assembled elements can be re-shaped. For example, the fastening means and attachment portion can be directly coupled via plastic deformation, crimping, shrink fit etc. However, preferably the coupling is achieved simply by correct alignment of the attachment portion and the fastening means. This means that no alteration or modification is necessary of either the head or base part in order to enable coupling to occur. Examples of such couplings are form fit, bayonet fixture or elastic deformation of the components.

Preferably the attachment portion and fastening means are directly coupled together by means of a snap fit connection. This is a form of elastic deformation and as such the base and head parts are coupled simply by bringing the attachment portion and fastening means into alignment. To form a snap fit coupling at least one of the attachment portion and fastening means must be resiliently flexible such that this can be distorted to allow the head and base parts to be moved into alignment before "springing" or "snapping" back towards or to its original shape to retain the components in their aligned position.

Preferably the attachment portion is located at the apical end of the head part. It is further preferable that the fastening means is located at the coronal end of the base part. In other words the head part does not comprise a further portion positioned apically of the attachment portion and the base part does not comprise any portion which is positioned coronally above the fastening means. The attachment portion and fastening means form the apical and coronal end surfaces respectively of the head and base parts. This eases construction of these components and minimises the overlap between the parts when in the coupled state. This enables the length of the base part to be kept short, hence reducing the bending forces exerted on this during use.

In accordance with conventional dental terminology, "apical" refers to the direction towards the bone and "coronal" to the direction towards the teeth. Therefore the apical end of a component is the end which, in use, is directed towards the jaw bone and the coronal end is that which is directed towards the oral cavity.

In the coupled state the base part should be able to freely rotate about its longitudinal axis at least over a partial angular range. This enables the base part to be rotated relative to the head part such that the implant connection means can engage the implant and hence secure the secondary component to this. Thus, the implant connection means of the base part is arranged to provide, through relative rotation to the implant, a secure axial fixation to this. In this way, as discussed previously, the secondary component can be fastened to the implant without the need for any additional fixation component, such as a basal screw. The implant connection means thus provides axial fixation to the implant, implemented via rotation.

In order to provide a coupling between the head and base part which is axially fixed but allows rotation, the head and base part can be connected by screw threads. It is preferable however for one of the attachment portion and fastening means to comprise at least one rail and for the other to comprise one or more runners shaped to engage said rail.

This is considered inventive in its own right and therefore, viewed from a further aspect the present invention provides a secondary component for connection to a dental implant having an internal bore, said secondary component comprising a head part and a base part, the head part comprising a coronal portion which in use protrudes from the dental implant, and, apical of the coronal portion, an attachment portion, the base part comprising implant connection means for connection to an implant and fastening means, wherein one of the attachment portion and fastening means comprises at least one rail, and the other comprises one or more runners shaped to engage said rail in a rotatable manner in order to axially join the head and base parts together, the head part further comprising a through passage extending from the coronal portion to the attachment portion and the base part comprising drive means which, when the head and base parts are coupled together, is in communication with this passage.

Preferred features of this aspect of the present invention correspond to those listed above and below in relation to the first aspect.

The rail can take the form of either a protrusion or a groove extending over an angular range in an internal or external surface of the head or base part. For example, the attachment portion or fastening means may comprise an annular wall extending around the circumference of the part and forming a hollow cavity. The rail is then formed in or on the interior wall. Alternatively the rail may be formed by a constriction, groove, widening or protrusion on the exterior surface of the head or base part. A single rail can be provided or multiple rails can be positioned at angularly spaced intervals, thus forming a "broken" or "dashed" rail.

The one or more runners are shaped to engage with the rail. In other words they comprise an indentation or protrusion having a profile that complements that of the rail. This enables the runners to abut against the rail, thus axially fixing the base part relative to the head part, but to move along this rail, thus providing the required relative rotation. The runners can be shaped to exactly inversely match the profile of the rail, thus giving an exact axial fixation, or they can have a profile that allows some axial play between the head and base part when coupled together. This latter option can be beneficial during seating of the secondary component within the implant.

In general the one or more runners have a lesser angular extension than the at least one rail, such that these can be moved along this. Thus, in any embodiment in which the at least one rail and the one or more runner have differing angular extents to one another, the feature having the smaller angular extent is labelled the "runner". Preferably the secondary component comprises more runners than rails. In a particularly preferred embodiment the component comprises a single rail and a plurality of runners shaped to engage the rail. It is however possible for both the rail and the runner to have the same angular extension, in particular when both rail and runner extend 360° about the longitudinal axis of the attachment portion and fastening means. In this case either component could be considered as the rail or the runner.

The runners can take the form of axially extending arms having at their distal ends an indentation or protrusion having a profile which complements the profile of the rail.

When the rail is formed in an interior cavity of the head or base part, the runners may comprise axially extending arms arranged for insertion into this cavity. Alternatively a central stem could be provided, having at its distal end radially extending runners.

Preferably however the at least one rail is formed on the exterior surface of the attachment portion or fastening means. The one or more runners therefore at least partially surround the rail when in the coupled state.

The one or more runners can comprise a plurality of evenly spaced identical arms, for example two, three or four. In a preferred embodiment six or more arms are provided, more preferably at least ten arms, for example twelve. Preferably however less than fifteen arms are provided to ensure these have adequate strength. These arms are evenly spaced about the longitudinal axis of the attachment portion or fastening means, depending on which component comprises said runners.

In a further preferred embodiment however the one or more runners comprise one or more axially extending arms which together form a "horseshoe" or "C" shaped side wall. Such a side wall can be created by a single arm which extends about an angle of at least 180°. Alternatively the side wall can be created by a plurality of closely spaced, axially extending arms spaced such that the gap between one pair of axially extending arms is greater than the gap between the other pairs of axially extending arms. In effect this creates a "broken" or "dashed" side wall. Preferably the side wall extends over an angle of greater than 180°, preferably greater than 200°. A particularly preferred angular range for the side wall is between 190-220°.

The provision of a side wall creates a lateral opening and enables the attachment portion and fastening means to be coupled together by relative lateral movement of the head and base part such that the at least one rail is pushed through the lateral opening into the hollow space defined by the side wall. This provides a simple connection method. The provision of a broken side wall provides a greater degree of flexibility, increasing the ease with which the attachment portion or fastening means can be pushed through the lateral opening.

In a particularly preferred embodiment the one or more runners comprise three axially extending arms, which together form a "C" shape, the middle arm extending over an angle at least twice that of each of the end arms, more preferably between 10 and 20 times the angle of each end arm. In this way the majority of the runner surface is provided by a single arm, which increases its stability, however the end portions of the side wall, formed by the end arms, have an increased flexibility which assists in connecting the head and base parts together. In one preferred embodiment the end arms each extend over an angle of between 10 and 15° while the middle arm has an angular extension of approximately 180°.

More generally, it is preferred that one of the attachment portion and fastening means comprises a lateral opening shaped to allow insertion of the other of the attachment portion and fastening means such that coupling of the components occurs via relative lateral movement.

This is considered inventive in its own right and therefore, according to another aspect the present invention provides a secondary component for connection to a dental implant having an internal bore, said secondary component comprising a head part and a base part, the head part comprising a coronal portion which in use protrudes from the dental implant, and, apical of the coronal portion, an attachment portion, the base part comprising implant connection means for connection to an implant and fastening means, wherein one of the attachment portion and fastening means comprises a lateral opening shaped to allow insertion of the other of the attachment portion and fastening means such the head and base part can be connected in a rotatable manner via relative lateral movement, the head part further comprising a through passage extending from the coronal portion to the attachment portion and the base part comprising drive means which, when the head and base parts are connected together, is in communication with this passage.

The lateral opening may be defined by a "C" shaped annular side wall as described above.

Preferably the attachment portion and fastening means are directly coupled together.

Further preferred features of this aspect of the present invention correspond to those listed above and below in relation to the first aspect.

Preferably it is the attachment portion which comprises at least one rail located on its exterior surface. This prevents the need for the head part to comprise a cavity or thin walled arms and thus increases the strength of this component. Preferably the rail is located on a section of the attachment portion having a narrower diameter than the apical end of the coronal portion. In other words the rail has a smaller diameter than the apical end of the coronal portion. The narrowed diameter of the attachment portion allows the fastening means to at least partially surround the rail without increasing the overall diameter of the secondary component. This enables the secondary component of the present invention to be used with pre-existing implants.

Preferably the rail is in the form of a continuous groove. In the embodiment above this can be formed by the narrowed diameter section of the attachment portion itself or a groove can be created within this narrowed diameter section. In alternative embodiments a rail in the form of a continuous protrusion can be located on the narrowed diameter section.

When the attachment portion comprises a rail the fastening means preferably comprises at least one runner in the form of an axially extending arm having a distal end shaped to complement the rail. When the rail is formed by a groove the distal end of the arm therefore comprises a protrusion shaped to allow accommodation within this groove. The axially extending arm(s) preferably form a "C" shaped side wall or a plurality of arms evenly spaced about the longitudinal axis as discussed above.

As also discussed above it is preferable that the head and base parts are coupled together by a snap fit connection. Preferably therefore the one or more runners are resiliently flexible in order to enable a snap fit connection to the one or more rail. However, other connection methods are possible, for example the runner(s) can be coupled to the rail(s) by plastic deformation after the rail(s) and runner(s) have been aligned.

When the one or more runners are resiliently flexible to enable a snap connection, it is particularly preferred that the one or more runners at least partially surround the rail. This enables the system to be designed such that, when the secondary component is connected to the implant, the external surface of the one or more runners are in close proximity or contact with the internal bore of the implant, or other part of the implant system. This prevents the possibility of any unwanted outward flexing of the runner(s), which could result in a loosening or decoupling of the head part. Alternatively or additionally, the protrusion or indentation of the runner(s) could be barb shaped, such that decoupling of the snap connection is resisted.

The attachment portion and fastening means can be configured to allow relative rotation between the head and base parts of 360°, or to enable only partial rotation. When only partial rotation is required the attachment portion and/or fastening means can be provided with stops to limit relative rotational movement. For example, when rails and runners are used the at least one rail can be provided with stops to limit movement of the runner(s). When the rail is provided in the form of one or more grooves, these can subtend an angle less than 360°, wherein the areas between the grooves act as stops to limit relative rotation. Alternatively protruding flanges can be positioned at the ends of the rail against which the runner(s) will abut.

The drive means of the base part is, when the head and base parts are coupled together, in communication with the through passage of the head part. This enables a driving tool to be inserted through this passage to engage with the drive means and rotate the base part relative to the head part. In some embodiments the drive means comprises a protrusion that lies below or within the through passage when the two part secondary component is coupled together. In other embodiments the drive means comprises an indent. The drive means can be any non-circular shape that is capable of transmitting torque to the base part, such as cross-shaped, bar-shaped, star shaped or TORX® shaped. Thus, the drive means preferably has a non-circular cross-section capable of transmitting torque to the base part. Preferably the drive means is formed on an internal wall of the base part, i.e. the drive means is formed by an indent, hollow or passage rather than a protrusion, such that the driving tool is inserted into rather than over the drive means.

In a particularly preferred embodiment the drive means comprises a passage extending along the longitudinal axis of the base part. In the present context, a passage is distinguished from an indent by the fact that the depth of a passage is greater than its width, whereas the reverse is true for an indent. This increases the length over which torque transmission occurs and thus creates a better force distribution. Preferably the drive means has a polygonal cross-section. Most preferably, for ease of manufacture, the drive means comprises a passage having a square or rectangular cross-section. Preferably the corners of the polygonal cross-section are rounded. In the case of a rectangular cross-section the rectangle can be rounded over the entire length of each short side, leading to a cross-section comprising two opposing planar sides interconnected by curved sections. Preferably the passage extends at least 0.5 mm into the base part and may form a through passage.

The through passage of the head part must be dimensioned to allow both insertion and unhindered rotation of the drive tool. Preferably therefore this has a width at least equal to the greatest width of the drive means. Preferably the passage is rotationally symmetric as this enables the passage to be as narrowly dimensioned as possible.

Preferably the through passage has a width of less than 2 mm, preferably between 0.8 & 1.5 mm. This offers a significant decrease in width in comparison to systems using a standard basal screw, which has a head diameter of approximately 2.5 mm.

In addition to the fastening means and drive means, the base part further comprises implant connection means for connection to an implant. As discussed above, the implant connection means is designed to enable connection to the implant in an axially secure manner via relative rotation between the base part and implant. Thus, the implant connection means is a means for axially fixing the secondary component to the implant upon relative rotation.

Preferably the implant connection means is located apical of the fastening means, although it is also possible for these constituents of the base part to overlap. For example, the fastening means may comprise a central stem and the implant connection means may take the form of an annular wall surrounding the central stem, wherein in the coupled state the attachment portion fits into the annular gap between these means. Alternatively, the fastening means may form a part of the implant connection means. For example, when the fastening means takes the form of an annular wall, the interior of which engages with the attachment portion, threads or other markings may be formed on the exterior of the wall which engage with and fasten to the internal bore of the implant.

As the base part is directly coupled to the attachment portion of the head part it is not necessary for this to be passed through the through passage in the head part. Hence, the diameters of the base part and the through passage are not mutually dependent and so the through passage can be narrowed. Therefore, according to a preferred embodiment the through passage of the head part is narrower than the diameter of the implant connection means. Preferably, this passage is narrower than the smallest diameter of the base part. Because the base part cannot be passed through the through passage of the head part, the secondary component must always be pre-assembled prior to attachment to the implant. This is in contrast to standard basal screw systems in which the basal screw can be inserted through the secondary component once this is positioned on the implant.

The through passage of the head part extends from the coronal portion to the attachment portion and is open at either end. As one end of the passage is located in the coronal portion, this is accessible after the secondary component has been positioned in the implant.

In order to communicate with the drive means of the base part, the through passage can extend through the attachment portion, or it may open into a cavity or hollow in the attachment portion. Whether the through passage extends to the apical end of the head part or only to the attachment portion depends on whether the attachment portion has been designed to surround, or be surrounded by, the fastening means of the base part. In order to keep the hollow space within the head part to a minimum, it is preferable that the fastening means couples to the exterior of the attachment portion. In this way the attachment portion does not need to comprise an internal cavity. This is advantageous as such a cavity would decrease the volume of the head part. The attachment portion is therefore preferably at least partially surrounded by the fastening means when the head and base parts are coupled together. In such embodiments therefore none of the base part is accommodated within the head part and the through passage extends to the apical end surface of the head part.

This is considered to be inventive in its own right and therefore, viewed from another aspect, the present invention provides a secondary component for connection to a dental implant having an internal bore, said secondary component comprising a head part and a base part, the head part comprising a coronal portion which in use protrudes from the dental implant, and, apical of the coronal portion, an attachment portion, the base part comprising implant connection means for connection to an implant and fastening means, wherein the fastening means is arranged to fasten to the exterior of the attachment portion in a rotatable manner, the head part further comprising a through passage extending through the head part and the base part comprising drive means which, when the head and base parts are fastened together, is in communication with this passage.

Preferred features of this further aspect of the present invention correspond to those listed above and below in relation to the first aspect.

The through passage can be inclined with respect to the longitudinal axis of the attachment portion and may even be curved, however preferably the passage extends along the longitudinal axis of the attachment portion.

The longitudinal axis of the coronal portion may be co-axial with the longitudinal axis of the attachment portion or it may be angled with respect to this. This is particularly true when the secondary component is an abutment, as the angulation of the coronal portion will depend on the desired orientation of the final prosthesis. The longitudinal axes of the attachment portion and base part are however co-axial and thus allow for the base part to be rotated about its longitudinal axis when coupled to the attachment portion.

The implant connection means is designed and dimensioned in line with the implant design in order to enable the base part to be securely fastened to the implant. In one preferred embodiment the implant connection means comprises an external thread for cooperation with an internally threaded implant bore. When the threads of the base part are engaged with the threads of the implant, the base part, and hence the coupled head part, are axially secured to the implant, i.e. they cannot be removed from the implant until the threads have been disengaged. However, in another preferred embodiment the implant connection means comprises angularly spaced nubs or grooves, which cooperate with complementary grooves or nubs in the implant bore, such that the implant and abutment can be connected together by way of a bayonet fitting. The term "bayonet fitting" is a well known term which refers to a connection comprising a groove extending firstly in an axial direction and then in a circumferential direction to form an approximately "⌐" shaped groove. The axially extending part of the groove provides access to the circumferential part and often contains a restriction such that a pin or other protrusion must be forced through the axial part of the groove into the circumferential passage such that it is then retained in the circumferential part of the groove. This results in the "push-twist" action that characterises a bayonet fitting. In some cases the circumferential part of the groove may follow a helical or slanted path and/or itself have restrictions such that the pin can be retained within a section of this groove. In the present invention the base part can be designed to comprise either the grooves or pin of the bayonet fitting.

In another embodiment the implant connection means may comprise an apically extending stem at the distal end of which is a disk having a greater diameter than the stem and a non-circular cross-section, such as a polygon. The implant bore comprises a section having a corresponding cross-section to the disk and, apical of this section, a chamber having a greater cross-sectional area. When the base part and implant are correctly aligned the disk can be inserted through the section of implant bore having the same cross-section and into the chamber. The base part is then rotated such that the disk moves out of alignment with the implant bore such that the base part cannot be removed from the chamber.

The rotational play between the head and base parts, when coupled together, must be sufficient to allow the implant connection means to fully engage with the implant. Preferably the coupling between the base and head parts allows unhindered relative rotation about 360°. In some embodiments however, for example in bayonet fittings, the connection may allow only partial relative rotation, preferably at least 45°, more preferably 90°-180°.

The present invention allows an abutment or other secondary component to be created in which only the base part needs to be rotated in order to connect the implant and secondary component together. This enables the angular position of the head part relative to the implant to be set prior to fixation of the secondary component within the implant.

Preferably therefore the head part comprises anti-rotation means, for co-operation with an implant. In this manner the head portion can be exactly positioned relative to the implant, whilst still allowing the secondary component to be rotationally secured to the implant by way of the base part. As discussed above, an anti-rotation means has a non-circular cross-section adapted to fit in a non-rotational manner to a complementary anti-rotation means of the implant.

Preferably the anti-rotation means is arranged for cooperation with the interior bore of the implant. Thus, the anti-rotation means is formed on an external surface of the head part. Preferred shapes for the anti-rotation means comprise a polygonal shape, such as a hexagon or octagon, which matingly matches a polygonal cavity in the implant, or grooves or planar surfaces shaped to co-operate with protrusions in the internal bore of an implant. Conversely the anti-rotation means of the head part can comprise protrusions for insertion into grooves or indents in the implant. It should be noted that the shapes of the implant and secondary component anti-rotation means do not need to be identical as long as these can engage one another in a non rotational manner. For example, the implant may comprise a square cavity and the secondary component an octagonal section. Any known anti-rotation means can be used.

In order to minimise the number of interfaces which are exposed to body tissue, it is preferable that the connection between the head and base parts is located, when the secondary component is mounted to the implant, within the internal bore of the implant. This reduces the number of microgaps on the implant-secondary component surface. Therefore preferably the head part is shaped to sealingly engage with the coronal end of the implant. The sealing engagement can be formed by the coronal end of the attachment portion. In other words the external geometry of the coronal end of the attachment portion is complementary to the cross section of the coronal end of the implant bore, such that when the attachment portion is inserted into the bore this coronal end seals the implant bore. Alternatively or additionally the apical end of the coronal portion of the head part can be shaped to abut against the coronal surface of the implant which surrounds the implant bore. As the base part is coupled to the apical end of the head part, the interface between attachment portion and fastening means is thus located within the implant.

In a preferred embodiment the coronal end of the attachment portion comprises a tapered section that tapers outwards in the coronal direction to join the apical end of the coronal portion. This tapered section can engage with an equivalent tapered portion of the internal bore of the implant to provide a good seal between these two components.

When the head part comprises anti rotation means this is preferably located in and/or apical of the tapered section.

Preferably the base part couples to the head part apical of the anti-rotation means. This reduces the length of the base part and means that the anti-rotation means and sealing engagement are pulled down onto the implant rather than pushed down. The reduced length of the base part reduces the bending forces on this component.

The coronal portion of the head part, in use, extends coronally from the implant into the soft tissue. In many cases the coronal portion is sized to extend through the soft tissue into the patient's oral cavity. In a preferred embodiment the secondary component is an abutment. In such instances the coronal portion is designed to be suitable for supporting a dental prosthesis. It thus extends, in use, through the soft tissue and into the oral cavity to provide a core support for a prosthesis. The coronal portion may comprise a cylindrical or conical post extending coaxial to the longitudinal axis of the attachment portion or at an angle to this. The apical region of the coronal portion may further comprise, below the cylindrical or conical post, an outwardly tapered section which ends in a platform that can be wave or scallop shaped or perpendicular to the axis of the attachment portion. This portion helps to shape the gingiva around the abutment and to mimic a natural tooth emergence profile. The platform offers support to the final prosthesis. Alternatively the coronal portion can be individually shaped according to the specific oral situation of the patient. Such shaping can be achieved, e.g., through CAD-CAM technology. In use the prosthesis can be screwed, glued or even directly veneered onto the coronal portion. The abutment can be a permanent or temporary abutment.

In other embodiments the secondary component can be, for example, a healing cap or a matrix for a removeable prosthesis, wherein in each case the coronal portion is shaped in a known manner which allows the secondary component to perform its function.

The two parts of the secondary component can be made of any suitable biocompatible material, for example titanium, metal alloy, plastic, ceramic or composite material. The two parts can be made from the same material or can be made from different materials. For example, in one embodiment the head part is formed from a ceramic or plastic material and the base part from a metal material, e.g. titanium or titanium alloy. Forming the head part from ceramic or plastic is particularly beneficial as this can be coloured in an aesthetically pleasing manner, while forming the base part from metal enables a metal-to-metal connection between the secondary component and a metal implant, although such a component could equally well be connected to a ceramic implant. In the above preferred embodiment the fastening means preferably comprises one or more arms forming runners. As metal is more flexible than ceramic it is beneficial to create the arms in the metal base part. These can be snapped, clamped, shrunk fit or otherwise coupled about the attachment portion. This enables the shape of the ceramic or plastic attachment portion to be less complex, e.g. comprising a single rail on its external surface, and solid except for the through passage.

According to another aspect the present invention provides a dental implant system comprising a secondary component as hereinbefore described and a drive tool comprising a shaft dimensioned for insertion into the through passage of the head part and comprising at its distal end a drive element for form fit connection to the drive means of the base part.

Preferably the drive element is polygonal in shape, more preferably square or rectangular, and has the same cross-sectional shape as the drive means of the base part. In some embodiments the shaft as a whole may have the cross section of the drive element. Preferably the shaft and drive element have a diameter of 0.8-1.5 mm. As the drive tool only remains in the mouth for a short time, there are less restrictions on material choice. Therefore a material with a high torsional strength can be chosen such that, despite its narrow diameter, the tool can transfer sufficient torque to the implant without distortion or sheering. Suitable materials include stainless or hardened steel, fibre-reinforced polymers or titanium alloy.

This tool can be inserted through the passage of the head part for engagement with the drive means of the base part such that torque can be transmitted to this part and the secondary component fastened to the implant via rotation of the base part. In some embodiments the shaft could be flexible to allow this to be inserted into a curved passage.

Preferably the system further includes an implant comprising an internal bore, this internal bore comprising, towards its apical end, a screw thread, the internal bore being dimensioned to receive the base part and the attachment portion of the head part. Preferably the internal bore further comprises, coronal of the screw thread, anti-rotation means for cooperation with the head part of the secondary component and, coronal to the anti rotation means, a tapered section. Preferably the head and base part of the secondary component are configured such that, when coupled together and inserted into the implant, the base part is completely contained within the internal bore.

Viewed from another aspect the present invention provides a combination of a secondary component as herein before described and a implant as herein before described.

More generally, a further aspect of the present invention provides a combination of a secondary component as herein before described and an implant, said implant comprising an internal bore having a complementary structure to the implant connection means of the base part, such that rotation of the implant connection means relative to the implant structure results in engagement between the base part and the implant in order to axially secure the secondary component to the implant.

Preferred features of this further aspect of the present invention correspond to those listed above.

BRIEF DESCRIPTION OF THE DRAWINGS

Preferred embodiments of the present invention will now be described, by way of example only, with reference to the accompanying figures, in which.

DETAILED DESCRIPTION

Figure 1:
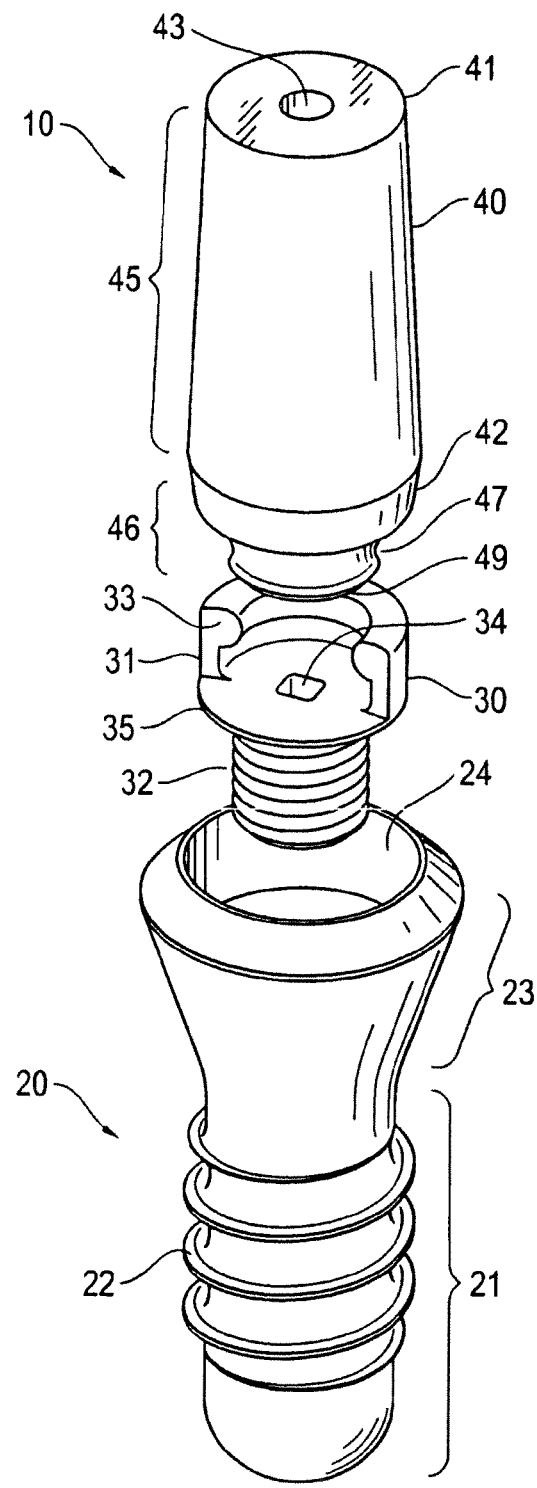
FIG. 1 shows a perspective, exploded view of a two part abutment according to an embodiment of the present invention and an implant.

FIG. 1 shows a two part abutment 10 in exploded perspective view, together with an implant 20. The implant 20 is a standard anchoring part of a two part implant system. It comprises a generally circular cylindrical section 21 with an exterior helical thread 22. In use this section 21 is inserted into the bone, wherein the thread 22 helps to provide primary stability. In the present embodiment the implant 20 is a so-called "tissue level" implant as in use it is positioned such that the uppermost part of the implant protrudes out of the bone and into the soft tissue. Implants which are fully positioned within the bone are known as "bone level" implants.

The implant 20 shown in FIG. 1 comprises an outwardly tapered coronal section 23 which in use is surrounded by soft tissue. In this example the tapered section 23 is smooth, to prevent bacterial infection, however it is also possible for this surface to be textured or surface treated in a known manner to enhance adhesion of the soft tissue to the surface. In a similar manner cylindrical section 21 can also be surface treated in a known manner, e.g. by acid etching or plasma spraying, to enhance osseointegration.

The external shape and texturing of the implant 20 are not relevant as regards the present invention and any known design can be used.

From the coronal end of the implant 20 an internal blind bore 24 extends longitudinally into the implant. This blind bore 24 acts as a socket, into which abutment 10 can be inserted. Other secondary components, such as healing caps, can also be inserted into this bore. Although not visible in FIG. 1 the blind bore comprises a threaded portion towards its apical end.

Abutment 10 comprises two separate components: head part 40 and base part 30. Head part 40 mainly consists of a coronal portion 45. This is shaped to extend out of the implant 20 and through the soft tissue to provide a support for a dental prosthesis. The coronal portion 45 is shown here as a frusto-conical post. However, any standard abutment design can be used, for example, the post can be angled and/or comprise a shoulder in its apical region.

Apical of the coronal portion 45 attachment portion 46 is provided. This consists of tapered section 42 and, apical of this, a section of narrowed diameter which forms a continuous groove 47. This groove 47 acts as a rail.

Head part 40 is a monolithic structure, i.e. integrally formed, and solid except for a narrow circular cylindrical through passage 43, which extends along the longitudinal axis of attachment portion 46, which in this case is coaxial with the longitudinal axis of the coronal portion 45. Passage 43 is open at either end and runs from the coronal end 41 to the apical end 49 of the head part 40. The head part 40 can be formed of any suitable biocompatible material, such as ceramic or titanium alloy.

Base part 30, also an integral structure, comprises a circular platform 35. From the underside, or apical end, of this platform extends screw thread 32, which is dimensioned to engage with the internal thread of the implant bore 24. Extending from the upper, or coronal end of platform 35 is fastening means, which takes the form of a runner 31. This runner 31 consists of an axially extending arm which extends circumferentially about platform 35 over an angle of at least 180°. The runner 31 therefore forms a C-shaped side wall. At the distal end of the runner 31 is an inwardly facing nub 33 which has a complementary shape to the groove 47 of the head part 40. The complementary shapes of the nub 33 and groove 47 enable these components to be directly coupled together in an axially secure manner. Runner 31 has enough flexibility to enable this to be pushed onto the attachment portion 46 in a lateral direction, i.e. perpendicular to the longitudinal axis of the abutment 10. No additional component is required to secure this snap connection between the head and base parts. Nor does either the attachment portion or fastening means need to be modified to couple the head and base parts together. Instead in this embodiment the direct coupling occurs through elastic deformation of the fastening means. Once connected the smooth continuous nature of groove 47 enables the base part 30 to be rotated 360° relative to the head part 40.

At the centre of platform 35 there extends a square passage 34. This extends along the longitudinal axis of the base part 30, which is coaxial to the head part 40 such that, when the head part 40 and base part 30 are coupled in the above described fashion, square passage 34 aligns with the cylindrical passage 43 of the head part 40. The diagonal length of square passage 34 is at most equal to the diameter of passage 43.

As discussed above, the head part 40 and base part 30 are designed such that these can be axially fixed together while still being rotatable relative to one another. This enables the base part 30 to be rotated relative to the head part 40 and implant 20, in order to threadedly connect abutment 10 to the implant 20. This rotation of the base part is driven by a suitable tool which can be inserted through the passage 43 to engage with square passage 34. Due to the larger and rotationally symmetric design of the passage 43, the tool can freely rotate within this. The tool is designed however to engage in a non-rotational manner with the square passage 34, such that torque applied to the tool is transmitted to the base part 30, causing this to rotate and threadedly connect to the implant 20.

The two part abutment therefore enables a screw thread of suitable strength and dimensions to engage with an implant without the need to create a similarly dimensioned through hole within the abutment. Instead the though hole of the present invention is much narrower than the screw thread 32 and hence the stability and strength of the abutment is increased. This is made possible by the unique construction of the abutment, which allows the thread 32 to be directly attached to the base of the abutment.

Figure 2:
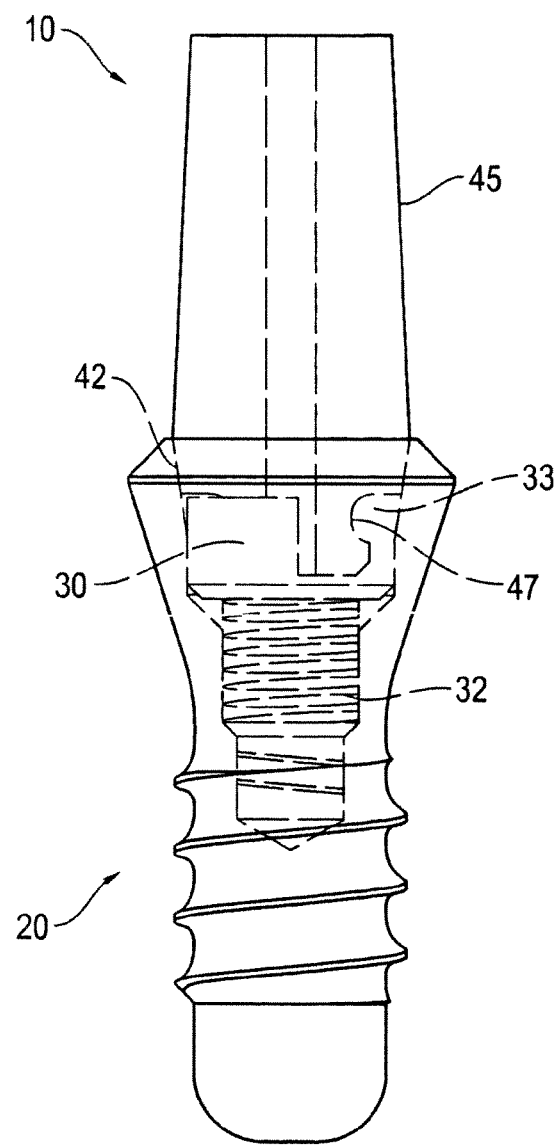
FIG. 2 shows a cross section through the assembled abutment and implant of FIG. 1.

FIG. 2 shows the abutment 10 and implant 20 when fully assembled and connected. As can be seen, nub 33 is in a form fit engagement with the groove 47. Thus, head part 40 and base part 30 of the abutment 10 are exactly fastened together in the axial direction. The connection between these two components does not prevent relative rotational movement however, as runner 31 can move along groove 47. Thus base part 30 can be rotated independently of the head part 40 in order to enable screw thread 32 to threadedly engage with the internal bore 24 of the implant 20.

When the abutment 10 is connected in this manner to the implant 20, the base part 30 is fully housed within the interior bore 24. The outer surface of runner 31 is in close proximity to the surface of the implant bore, thus preventing any outward flexing of the runner which could act to de-couple the head 40 and base 30 parts. The attachment portion 46 of the head part 40 comprises, coronal of groove 47, outward taper 42. This is shaped to complement the taper at the coronal end of the interior bore 24. Tightening of screw thread 32 draws the head part 40 downwards into the bore 24 and creates a frictional engagement between the two tapered sections. This provides a good, sealed connection between the implant 20 and abutment 10 and prevents the incursion of bacteria into the implant 20. The coronal portion 45 protrudes from the implant 20 and provides a transmucosal support for a final or temporary prosthesis.

Figure 3:
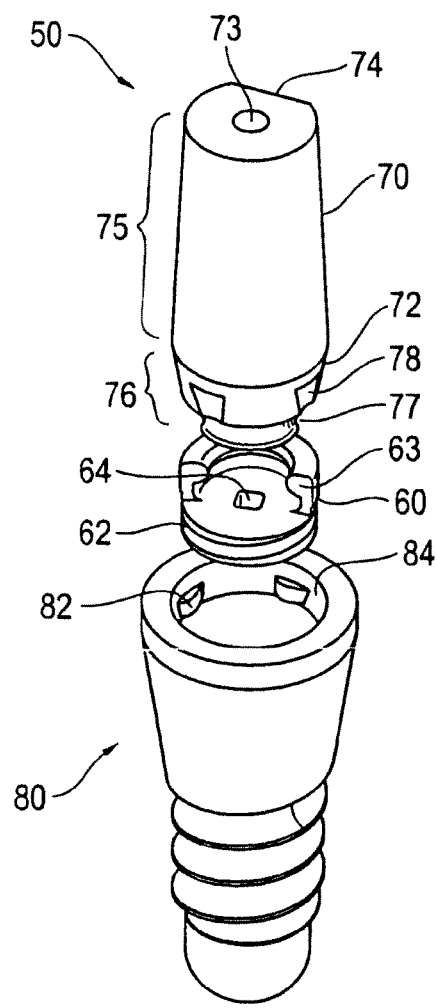
FIG. 3 shows a perspective, exploded view of a two part abutment according to a further embodiment of the present invention.

FIG. 3 shows an exploded view of an alternative embodiment of the present invention. Abutment 50 is very similar to that of the first embodiment, and comprises head part 70 and base part 60 which are axially fixed together by means of the nub 63 and groove 77 configuration described in detail in relation to FIG. 1. In this embodiment implant 80 has a slightly different external design to implant 20, but again comprises an internal bore 84 which contains a threaded section (not shown). Base part 60 of abutment 50 comprises a screw thread 62 dimensioned to threadedly engage with the screw thread of implant 80. In this embodiment this requires the screw thread 62 to have a wider diameter than that of FIG. 1. Furthermore in this embodiment the thread pitch is smaller, thus enabling the longitudinal length of the screw thread 62 to be shorter.

The main difference between the first and second embodiments however is the inclusion on head part 70 of anti-rotation means. These take the form of longitudinal indentations 78 formed in the taper 72 of attachment portion 76. The internal bore 84 of the implant 80 comprises matching protrusions 82. In use, as the abutment 50 is inserted into the implant 80, the indentations 78 slide over the protrusions 82 and hold the head part 70 in a non-rotational relationship with the implant 80. In this way the head part 70 can be positioned in a precisely defined angular relationship with the implant 80. This is of particular benefit when the abutment-implant assembly is intended for use with a single tooth prosethsis (crown). In such situations the coronal portion 75 typically comprises at least one planar surface 74 such that the prosthesis can be attached to this in a non-rotational manner. By precisely defining the angular position of the abutment, and hence this planar surface, the prosthesis can be modelled in advance, prior to final attachment of the abutment to the implant, without jeopardising the final look of the prosthesis.

The rotational relationship between the head part 70 and base part 60 enables the screw thread 62 to be tightened despite the non-rotational engagement between the head part 70 and the implant 80. As screw thread 62 does not need to be fed through the passage 73 of the abutment, as in prior art components, the diameter of the thread and passage are not mutually dependent. Thus, through passage 73 can be reduced in diameter, leading to a stronger coronal portion 75. In addition, as the base part 60 is coupled to the exterior of the head part 70 this head part 70 does not need to contain a cavity for accommodating the base part 60, which strengthens and simplifies the design of the head part 70. Further, as the base part 60 is coupled to the apical end of the head part 70 the length of the screw element (the base part) is reduced in comparison to prior art basal screws, and hence the bending forces experienced by this are reduced.

Figure 4:
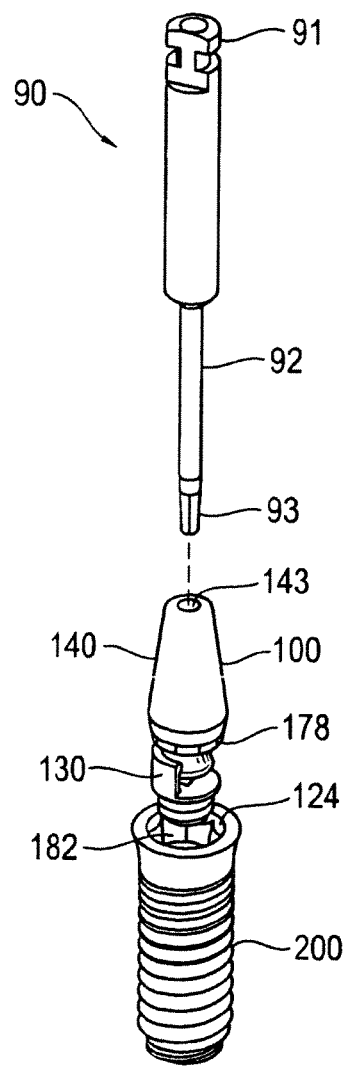
FIG. 4 shows a perspective view of a dental implant system according to a further embodiment of the present invention comprising a two part abutment, implant and drive tool.

FIG. 4 shows a further embodiment of the present invention, which comprises an implant 200 and abutment 100 that are functionally very similar to those described in relation to FIG. 1. Minor details of external design differ which have no relevance in the context of the present invention and so shall not be discussed.

The abutment 100 is shown in coupled form, with the head 140 and base 130 parts in axially fixed but rotational engagement. Once inserted into implant 200, tool 90 is used to rotate base part 130 and fasten the abutment 100 to the implant 200. Tool 90 comprises driven end 91, which is this embodiment takes the form of a standard latch for connection to a dental hand piece. Alternatively however the driven end 91 may be configured for attachment to a ratchet or can be shaped for direct manual rotation. Tool 90 further comprises a shaft 92 sized for insertion into through passage 143 of the abutment 100. The distal end 93 of shaft 92 has a square cross-section, which is shaped to engage with the passage 134 of the base portion of the abutment 100. The upper portion of the shaft 92 is, in the present case, circular cylindrical such that this can rotate relative to the passage 143 of the head portion 140. However, in alternative embodiments this may also be non-circular but dimensioned such that this can rotate unhindered within the through passage 143.

Tool 90 thus rotates the base part relative to the head part to connect the abutment to the implant.

Figure 5:
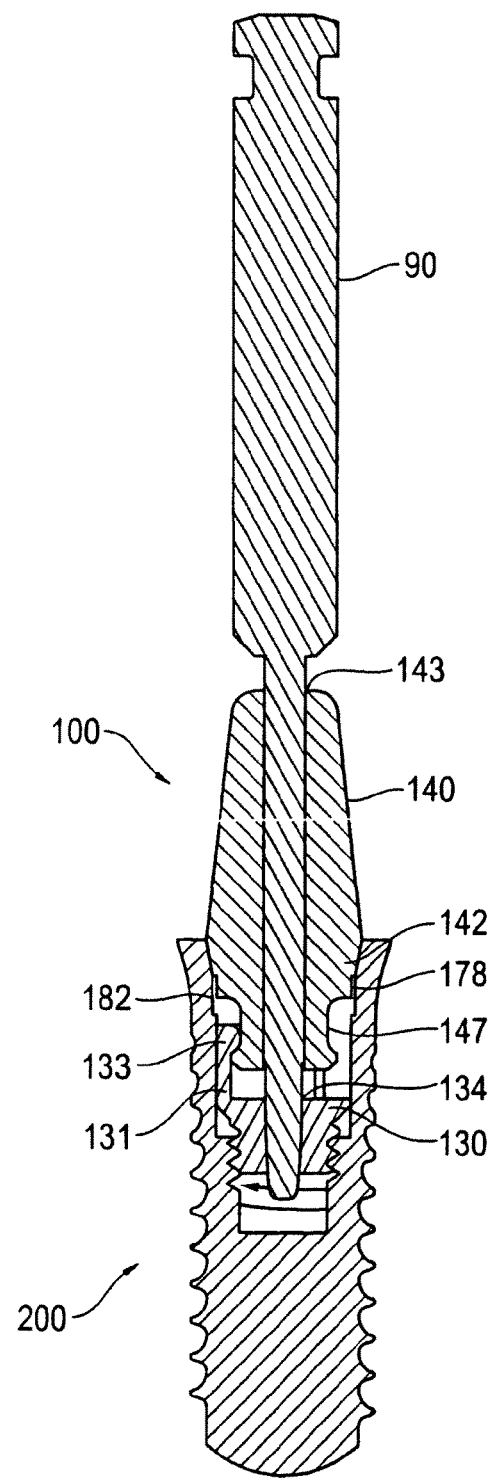
FIG. 5 shows a cross section of the assembled system of FIG. 4 with the tool in use.

FIG. 5 shows a cross section through the abutment 100, implant 200 and tool 90 when connected. This figure shows how the passages 143, 134 of the head 140 and base part 130 communicate with one another to allow the tool 90 to engage passage 134 and rotate the base part. In addition this figure also demonstrates how in this embodiment nub 133 of runner 131 does not exactly match the profile of groove 147. This enables some axial play between the head and base part when in the coupled state. In addition in this embodiment anti-rotation means are formed between the tapered section 142 and the groove 147. Section 178 of the attachment portion of head part 140 has a non-circular cross section, e.g. an octagon, which is accommodated in a non-rotational manner within complementary section 182 of the implant bore 124.

Figure 6:
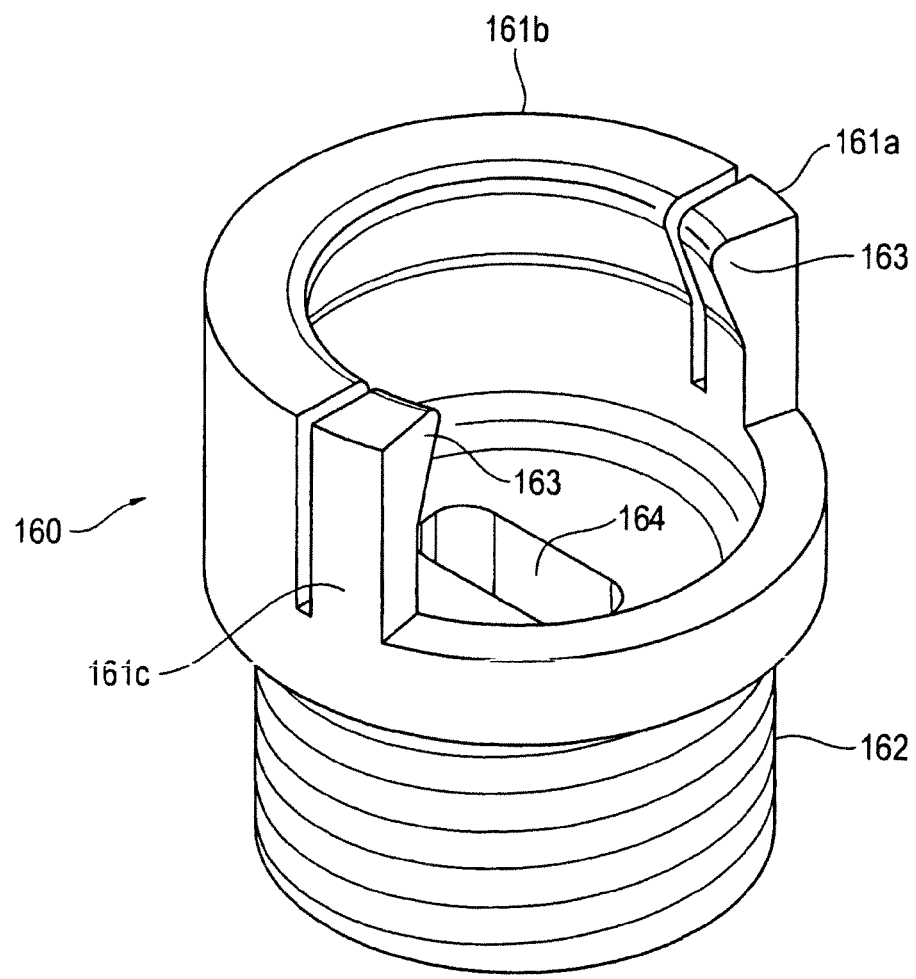
FIG. 6 shows a perspective view of a further embodiment of a base part according to the present invention.

FIG. 6 shows an alternative base part 160. The base part 160 comprises a screw thread 162 at its apical end and, at its coronal end a fastening means. The fastening means is formed by three axially extending arms which in combination form a "C" or "horseshoe" shaped side wall. These arms form runners 161a, 161b, 161c having at their distal ends nubs 163 shaped to fit within a groove on the head part. The splitting of the side wall to form a plurality of arms increases the flexibility of the side wall and eases the ability of the base part 160 to be snapped onto the head part. Central runner 161b has a much larger angular extension than the two side runners 161a, 161c. The lateral opening in the side wall, i.e. the gap between side runners 161a and 161c enables the head and base part to be coupled together via relative lateral movement.

Passage 164 is provided along the longitudinal axis of base part 160. In this embodiment the passage has the cross-sectional shape of a rectangle with rounded corners. The use of a rectangular cross section provides two relatively large surfaces for torque transfer and requires less reduction in volume than a similarly dimensioned square cross-section. A drive tool is provided which can engage with this passage 164 in order to rotate the base part 160.

Figure 7:
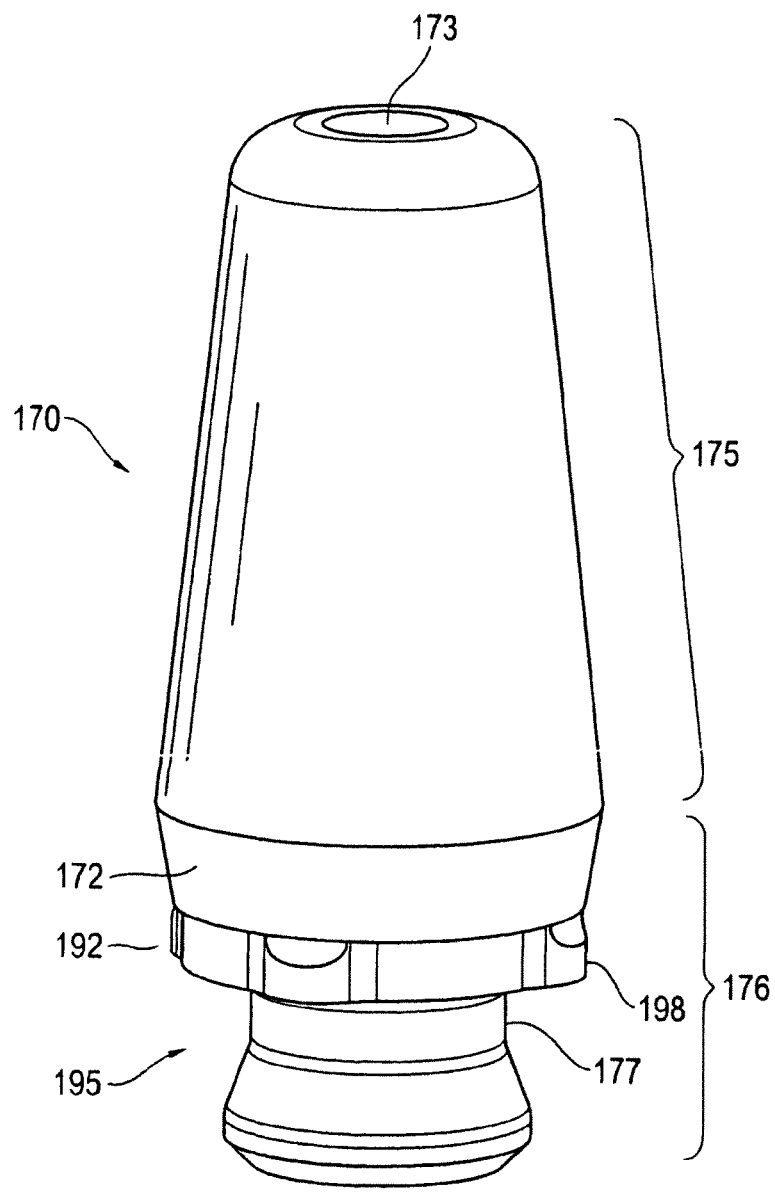
FIG. 7 shows a perspective view of a head part which can be coupled to the base part of FIG. 6.

FIG. 7 shows an alternative head part 170 that can be used with the base part 160 of FIG. 6. It comprises a coronal part 175 having a generally frusto-conical shape which is rounded at its coronal end. The attachment portion 176 comprises three distinct parts: a tapered section 172, an anti-rotation section 192 and a section of narrowed diameter 195. In contrast to the head part shown in FIG. 3, here the anti-rotation section 192 of the head part comprises a plurality of protrusions 198. These are dimensioned to fit within corresponding grooves of the implant bore. In this embodiment the protrusions 198 are located apical of the tapered section 172, however it is possible that in an alternative embodiment these could extend into the tapered section 172.

The section of narrowed diameter 195 forms a groove 177. Apical of this groove 177 the head part tapers outwards to form an abutment surface on which the runners can abut. Thus this apical most section 195 of the head part forms a rail. Through passage 173 extends from the coronal end to the apical end of the head part and is sized to allow passage of a drive tool for rotation of the base part which in use is directly coupled to the rail.

Figure 8A:
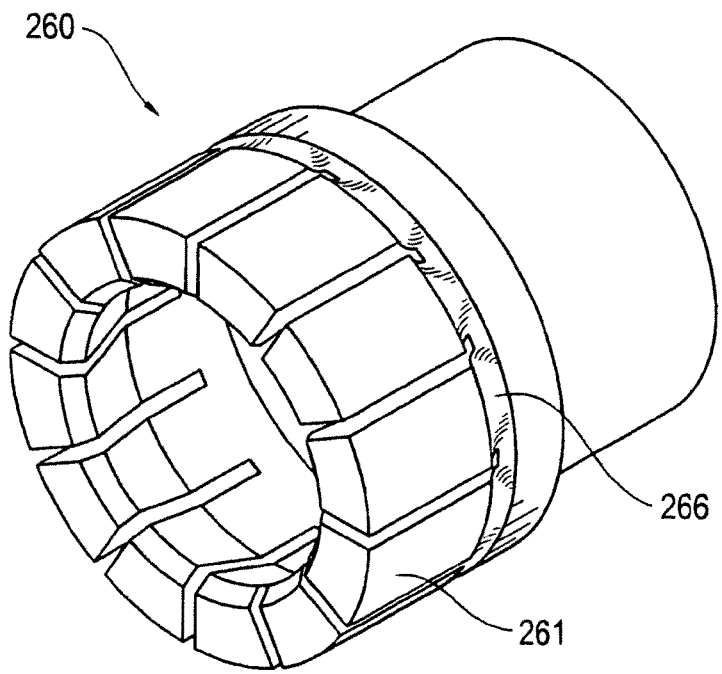
FIG. 8A shows a perspective view of an alternative base part of the present invention.
Figure 8B:
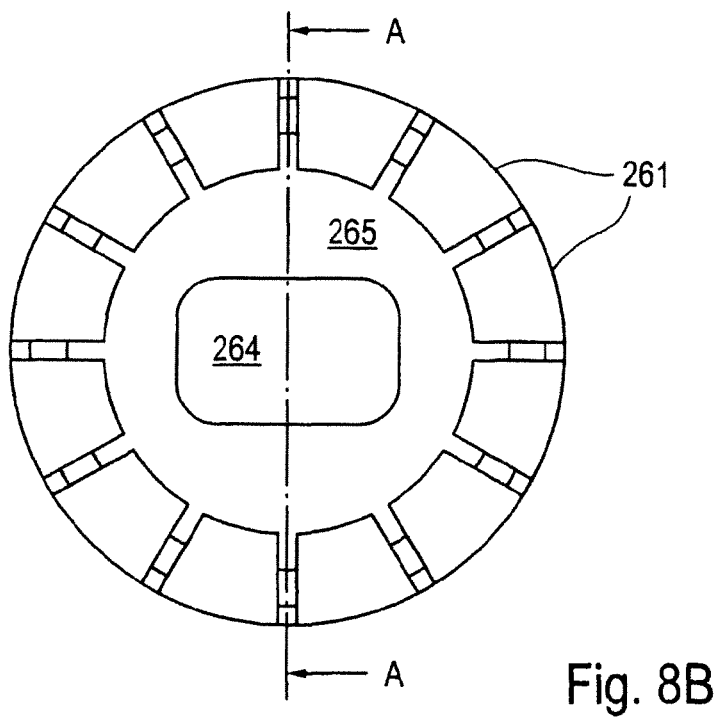
FIG. 8B shows a top plan view of the base part of FIG. 8A.
Figure 8C:
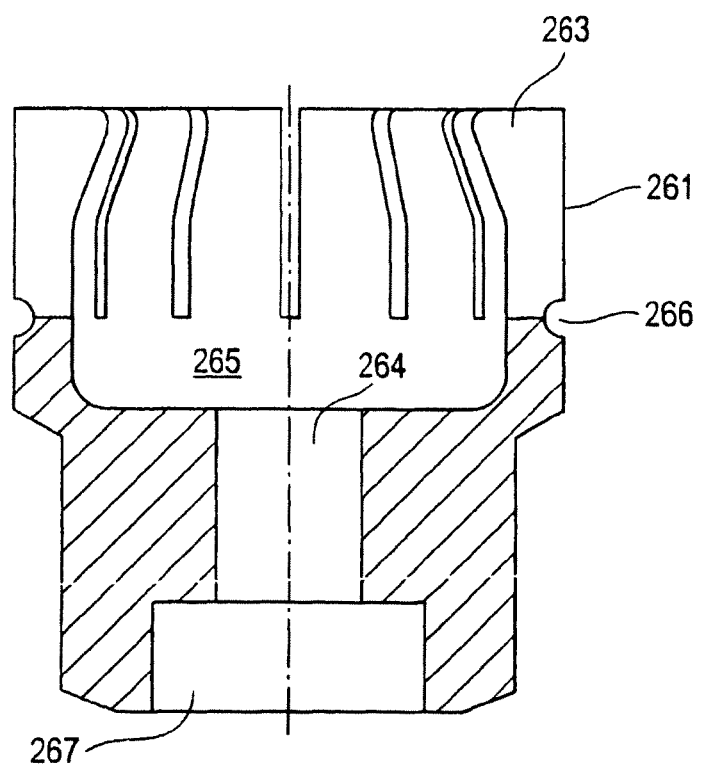
FIG. 8C shows a cross section along line A-A of FIG. 8B.

FIGS. 8A-C show an alternative base part that could be used with the head part of FIG. 7. This base part 260 is essentially identical to that of the base part 160 shown in FIG. 6 with the exception that arms 261 are evenly spaced about the longitudinal axis. Consequently, there is no lateral opening and instead the head and base parts are coupled together by forcing the attachment portion into the cavity 265 defined by the arms through relative axial movement of the two components. Arms 261 must therefore be flexible enough to bend outwards to enable passage of the attachment means through opening. Annular groove 266 on the exterior of the base part increases the outwards flexibility of the arms. When the groove 177 of the head part is brought into alignment with the nubs 263 of the base part the arms 261 are released to their original position and couple the head and base parts together.

Once again, as with FIG. 6, the drive means 264 is a passage in the shape of a rectangle with rounded corners, although other non-circular shapes could be chosen. Drive means 264 does not extend through the base part 260 but instead is widened at the apical end by counterbore 267. This counterbore 267 does not take part in the torque transfer process and is formed as a by-product of the manufacturing process. Apical of the arms the external surface of the base part comprises a thread (not shown) for engagement with the internal thread of an implant.

The above described embodiments are for illustrative purposes only and the skilled man will realize that many alternative arrangements are possible which fall within the scope of the claims. In particular, the base part may comprise alternative implant connection means, such as a bayonet system. Further, in some of the above described embodiments the base part comprises a side wall which partially encloses the continuous rail of the head part. In other embodiments the opposite construction is possible, where it is the base part that comprises at its coronal end a groove or protrusion around which a side wall of the head part can be snapped. The nubs of the runners could alternatively be grooves and the rail formed by a protrusion. In other embodiments the rail and runner configurations described above could form part of a plastic deformation connection rather than a snap fit connection. In such systems the runners would not need to flex to enable connection but instead could be engaged to the rail via crimping, clamping, shrink fit etc.

Unless expressly described to the contrary, each of the preferred features described herein can be used in combination with any and all of the other herein described preferred features.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

The invention claimed is:

1. A secondary component for connection to a dental implant having an internal bore, said secondary component comprising
a head part and a base part,
the head part comprising a coronal portion which in use protrudes from the dental implant, and,
apical of the coronal portion, an attachment portion,
the base part comprising implant connection means for connection to an implant and
fastening means,
wherein the attachment portion and fastening means can be directly coupled together in a rotatable manner in order to axially join the head and base parts together, while still enabling the base part to be rotated relative to the head part such that the implant connection means can engage the implant and secure the secondary component to this,
the head part further comprising a through passage extending from the coronal portion to the attachment portion and the base part further comprising drive means having a non-circular cross-section capable of transmitting torque to the base part which, when the head and base parts are coupled together, is in communication with this passage.

2. A secondary component as claimed in claim 1, wherein the head and base parts are each integral components.

3. A secondary component as claimed in claim 1, wherein the attachment portion and fastening means are arranged such that coupling is achieved solely through correct alignment.

4. A secondary component as claimed in claim 3 wherein the attachment portion and fastening means are directly coupled together by means of a snap fit connection.

5. A secondary component as claimed in claim 1, wherein the attachment portion is located at the apical end of the head part.

6. A secondary component as claimed in claim 1, wherein the fastening means is located at the coronal end of the base part.

7. A secondary component as claimed in claim 1, wherein one of said attachment portion and fastening means comprises at least one rail and the other of said attachment portion and fastening means comprises one or more runners shaped to engage said rail.

8. A secondary component as claimed in claim 7 wherein said at least one rail is formed on the exterior surface of one of said attachment portion and fastening means and the one or more runners partially surround the rail when in the coupled state.

9. A secondary component as claimed in claim 7 wherein the one or more runner takes the form of an axially extending arm having at its distal end an indentation or protrusion having a profile which complements the profile of the rail.

10. A secondary component as claimed in claim 9 wherein the one or more axially extending arms are evenly spaced about the longitudinal axis.

11. A secondary component as claimed in claim 7 wherein the attachment portion comprises at least one rail located on its exterior surface and the fastening means comprises at least one runner in the form of an axially extending arm having a distal end shaped to complement the rail of the attachment portion.

12. A secondary component as claimed in claim 11 wherein the at least one rail is located on a section of the attachment portion having a narrower diameter than the apical end of the coronal portion.

13. A secondary component as claimed in claim 7 comprising a single rail and a plurality of runners.

14. A secondary component as claimed in any of claim 7 wherein the rail comprises a continuous groove.

15. A secondary component as claimed in claim 1, wherein the implant connection means comprises an external thread.

16. A secondary component as claimed in claim 1 wherein the drive means comprises a passage extending along the longitudinal axis of the base part.

17. A secondary component as claimed in claim 1, wherein the through passage is narrower than the base part.

18. A secondary component as claimed in claim 1, wherein the fastening means can be directly coupled to the exterior of the attachment portion.

19. A secondary component as claimed in claim 1, wherein the head part comprises anti-rotation means, for co-operation with an implant.

20. A secondary component as claimed in claim 1, wherein the coronal end of the attachment portion comprises a tapered section that tapers outwards in the coronal direction.

21. A secondary component as claimed in claim 1, wherein the component is an abutment.

22. A dental implant system comprising
a secondary component as claimed in claim 1 and
a drive tool comprising a shaft dimensioned for insertion into the through passage of the head part and further comprising at its distal end a drive element for form fit connection to the drive means of the base part.

23. A dental implant system as claimed in claim 22, further comprising an implant comprising an internal bore, said internal bore comprising, towards its apical end, a screw thread and being dimensioned to receive the base part and at least the attachment portion of the head part.

24. A secondary component for connection to a dental implant having an internal bore, said secondary component comprising
a head part and a base part,
the head part comprising a coronal portion which in use protrudes from the dental implant, and, apical of the coronal portion, an attachment portion,
the base part comprising implant connection means for connection to an implant and fastening means,
wherein one of the attachment portion and fastening means comprises a lateral opening shaped to allow insertion of the other of the attachment portion and fastening means such the head and base part can be connected in a rotatable manner via relative lateral movement, the head part further comprising a through passage extending from the coronal portion to the attachment portion and the base part comprising drive means which, when the head and base parts are connected together, is in communication with this passage.

25. A dental implant system comprising a secondary component for connection to a dental implant and a dental implant, said secondary component comprising a head part and a base part, the head part comprising a coronal portion which in use protrudes from the dental implant, and, apical of the coronal portion, an attachment portion, the base part comprising implant connection means for connection to an implant and fastening means, wherein the attachment portion and fastening means can be directly coupled together in a rotatable manner in order to axially join the head and base parts together, while still enabling the base part to be rotated relative to the head part such that the implant connection means can engage the implant and hence secure the secondary component to this, the head part further comprising a through passage extending from the coronal portion to the attachment portion and the base part further comprising drive means having a non-circular cross-section capable of transmitting torque to the base part which, when the head and base parts are coupled together, is in communication with this passage, and said implant comprising an internal bore having a complementary structure to the implant connection means of the base part, such that rotation of the implant connection means relative to the implant structure results in engagement between the base part and the implant in order to axially secure the secondary component to the implant.

* * * * *

UNITED STATES PATENT AND TRADEMARK OFFICE
CERTIFICATE OF CORRECTION

| | | |
|---|---|---|
| PATENT NO. | : 9,095,398 B2 | Page 1 of 1 |
| APPLICATION NO. | : 14/117494 | |
| DATED | : August 4, 2015 | |
| INVENTOR(S) | : Courvoisier et al. | |

It is certified that error appears in the above-identified patent and that said Letters Patent is hereby corrected as shown below:

In the Claims

In column 20, line 64 (claim 24) after "such" insert --that--

In column 21, lines 5 and 6 (claim 21) delete "and a dental implant"

Signed and Sealed this
Twenty-second Day of December, 2015

Michelle K. Lee
*Director of the United States Patent and Trademark Office*